United States Patent [19]

Vidal et al.

[11] Patent Number: 5,749,893

[45] Date of Patent: May 12, 1998

[54] SURGICAL INSTRUMENT HAVING AN ARTICULATED JAW STRUCTURE AND A DETACHABLE KNIFE

[75] Inventors: Claude A. Vidal; Alan K. Plyley, both of Santa Barbara; Russell J. Redmond; Roger Lagerquist, both of Goleta, all of Calif.

[73] Assignee: United States Surgical Corporation, Norwalk, Conn.

[21] Appl. No.: 596,938

[22] Filed: Feb. 5, 1996

Related U.S. Application Data

[63] Continuation of Ser. No. 291,331, Aug. 17, 1994, abandoned, which is a continuation of Ser. No. 55,824, Apr. 30, 1993, abandoned.

[51] Int. Cl.$^6$ .................................................. A61B 17/068
[52] U.S. Cl. .................... 606/205; 227/176.1; 227/180.1
[58] Field of Search ................................ 606/205–208, 606/210, 142; 128/751; 81/347–351, 355, 112; 294/99.2; 227/180.1, 176.1, 178.1, 901

[56] References Cited

U.S. PATENT DOCUMENTS

| | | |
|---|---|---|
| 984,756 | 2/1911 | Frisch . |
| 1,274,669 | 8/1918 | Bohn .................................. 606/206 |
| 1,517,302 | 12/1924 | McNerney . |
| 1,659,112 | 2/1928 | Littlejohn . |
| 1,717,726 | 6/1929 | McGill . |
| 2,034,785 | 3/1936 | Wappler . |
| 2,968,041 | 1/1961 | Skold . |
| 3,232,150 | 2/1966 | Allegraud . |
| 3,269,630 | 8/1966 | Fleishcer . |
| 3,506,012 | 4/1970 | Brown . |
| 3,518,993 | 7/1970 | Blake . |
| 3,593,903 | 7/1971 | Astafiev ................................... 227/76 |
| 3,618,842 | 11/1971 | Bryan . |

(List continued on next page.)

FOREIGN PATENT DOCUMENTS

| | | |
|---|---|---|
| 0092300 | 2/1983 | European Pat. Off. . |
| 0211114 | 2/1987 | European Pat. Off. . |
| 0 286 921 | 10/1988 | European Pat. Off. . |
| 0 369 324 | 5/1990 | European Pat. Off. . |
| 0406724 | 1/1991 | European Pat. Off. . |
| 0 484 677 | 5/1992 | European Pat. Off. . |
| 0 505 138 | 9/1992 | European Pat. Off. . |
| 0 552 423 | 4/1993 | European Pat. Off. . |
| 0 598 202 | 5/1994 | European Pat. Off. . |
| 1 378 136 | 10/1964 | France . |
| 268621 | 6/1989 | Germany . |
| 51-149985 | 11/1976 | Japan . |
| 70697 | 1/1916 | Switzerland . |
| 599799 | 3/1978 | U.S.S.R. . |
| 728848 | 4/1980 | U.S.S.R. . |
| 1456108 | 2/1989 | U.S.S.R. . |
| 2 165 559 | 4/1986 | United Kingdom . |

OTHER PUBLICATIONS

Surgical Stapling, Gastic and Small Bowel Procedures, vol. I, by 3M (1988).
Surgical Stapling, Thoracic, Vascular and Esophageal Procedures, vol. II, by 3M )1988).
Surgical Stapling, Bariatric Procedures for Morbid Obesity, vol. III, by 3M (1989).

Primary Examiner—Michael H. Thaler

[57] ABSTRACT

A surgical instrument with articulated jaw structure includes a frame and two jaws. The jaws have proximal portions that are mounted to each other for movement in a substantially parallel relation between a fully open position wherein the jaws are separated for receiving tissue therebetween and an approximated position wherein the jaws are closer together. Preferably, the jaws are in the fully open position when the distal portion of at least one of the jaws is located in an extended position and are in the approximated position when the distal portion of the extended jaw or jaws is located in a retracted position. The surgical instrument may further include a detachable knife assembly and knife actuating mechanism.

10 Claims, 10 Drawing Sheets

U.S. PATENT DOCUMENTS

| | | | |
|---|---|---|---|
| 3,795,034 | 3/1974 | Strekopytov et al. . | |
| 3,828,791 | 8/1974 | Santos . | |
| 3,844,289 | 10/1974 | Noiles . | |
| 3,866,610 | 2/1975 | Kletschka . | |
| 3,882,854 | 5/1975 | Hulka et al. | 128/6 |
| 3,895,636 | 7/1975 | Scmidt . | |
| 4,038,987 | 8/1977 | Komiya . | |
| 4,106,508 | 8/1978 | Berlin . | |
| 4,111,206 | 9/1978 | Vishnevsky et al. | 128/305 |
| 4,122,856 | 10/1978 | Mosior et al. . | |
| 4,169,476 | 10/1979 | Hiltebrandt . | |
| 4,171,701 | 10/1979 | Walter et al. | 128/354 |
| 4,226,024 | 10/1980 | Westerberg et al. . | |
| 4,233,743 | 11/1980 | Flick . | |
| 4,243,047 | 1/1981 | Olsen . | |
| 4,265,021 | 5/1981 | Campbell . | |
| 4,273,129 | 6/1981 | Boebel . | |
| 4,312,363 | 1/1982 | Rothfuss et al. . | |
| 4,319,576 | 3/1982 | Rothfuss . | |
| 4,369,788 | 1/1983 | Goald . | |
| 4,383,634 | 5/1983 | Green | 227/19 |
| 4,424,811 | 1/1984 | Groot . | |
| 4,512,343 | 4/1985 | Falk et al. . | |
| 4,536,960 | 8/1985 | Muti . | |
| 4,566,620 | 1/1986 | Green et al. . | |
| 4,572,185 | 2/1986 | Rich . | |
| 4,580,712 | 4/1986 | Green . | |
| 4,590,936 | 5/1986 | Straub et al. . | |
| 4,603,693 | 8/1986 | Conta et al. . | |
| 4,646,751 | 3/1987 | Maslanka . | |
| 4,662,374 | 5/1987 | Blake | 81/349 X |
| 4,674,501 | 6/1987 | Greenberg . | |
| 4,711,240 | 12/1987 | Goldwasser et al. . | |
| 4,714,187 | 12/1987 | Green . | |
| 4,728,020 | 3/1988 | Green et al. | 227/19 |
| 4,760,848 | 8/1988 | Hasson . | |
| 4,784,137 | 11/1988 | Kulik et al. | 128/334 |
| 4,788,978 | 12/1988 | Strekopytov et al. . | |
| 4,848,637 | 7/1989 | Pruitt | 227/19 |
| 4,873,771 | 10/1989 | Wüst . | |
| 4,887,612 | 12/1989 | Esser et al. | 606/208 X |
| 4,931,058 | 6/1990 | Cooper . | |
| 4,941,623 | 7/1990 | Pruitt | 227/19 |
| 4,944,443 | 7/1990 | Oddseu et al. | 227/19 |
| 4,976,721 | 12/1990 | Blasnik et al. . | |
| 4,978,049 | 12/1990 | Green | 227/178 |
| 4,994,079 | 2/1991 | Genese et al. . | |
| 5,040,715 | 8/1991 | Green et al. | 227/176 |
| 5,071,430 | 12/1991 | de Salis et al. | 606/219 |
| 5,100,042 | 3/1992 | Gravener et al. . | |
| 5,171,249 | 12/1992 | Stefanchik et al. | 606/142 |
| 5,171,258 | 12/1992 | Bales et al. | 606/205 |
| 5,174,487 | 12/1992 | Rothfuss et al. | 227/176 |
| 5,176,690 | 1/1993 | Gross et al. | 606/205 X |
| 5,220,928 | 6/1993 | Oddsen et al. | 128/898 |
| 5,307,976 | 5/1994 | Olson et al. | 227/178 |
| 5,308,357 | 5/1994 | Lightman | 606/205 |
| 5,318,221 | 6/1994 | Green et al. | 227/128 |
| 5,332,142 | 7/1994 | Robinson et al. | 227/178 |
| 5,336,232 | 8/1994 | Green et al. . | |
| 5,358,506 | 10/1994 | Green et al. | 606/151 |

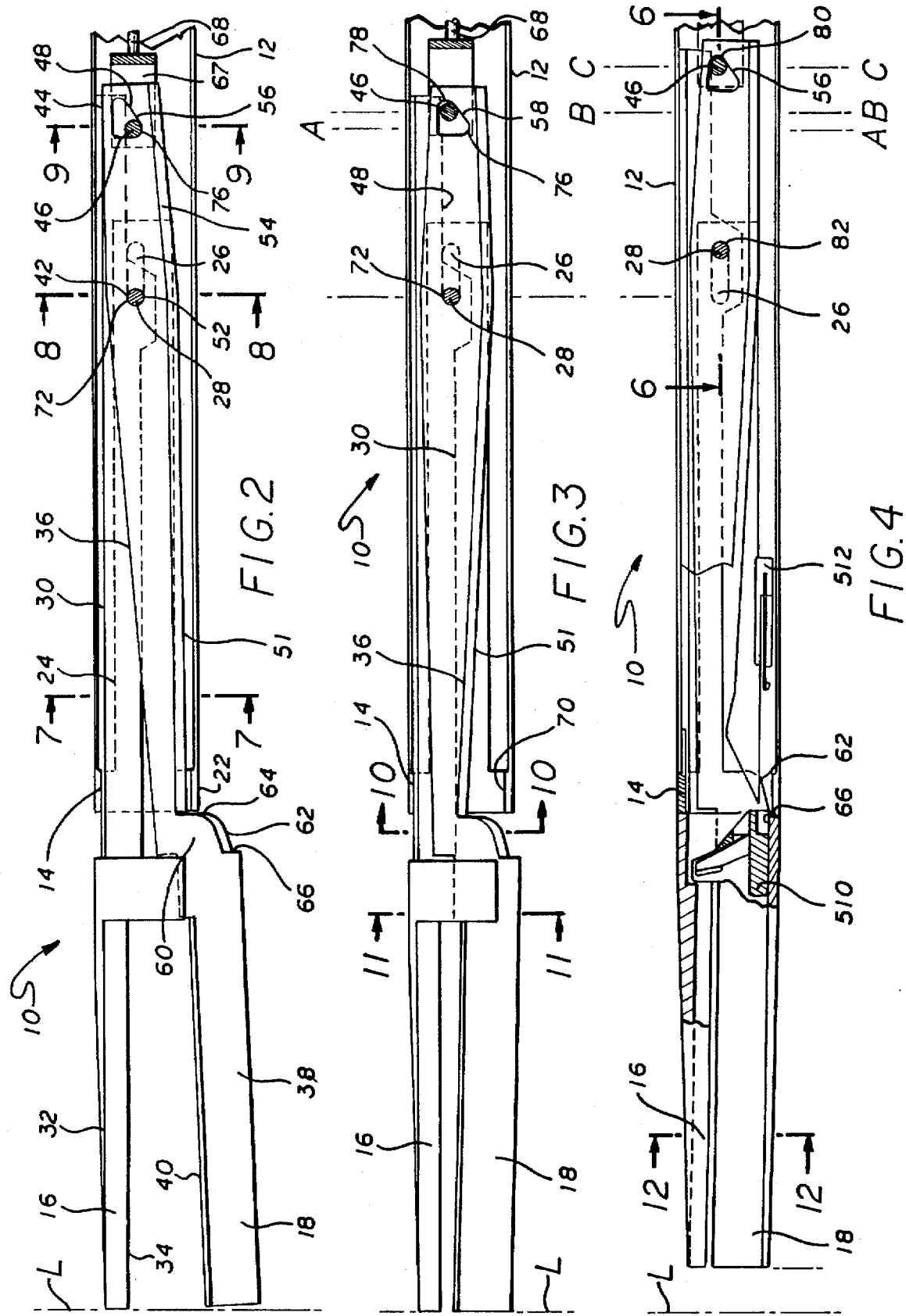

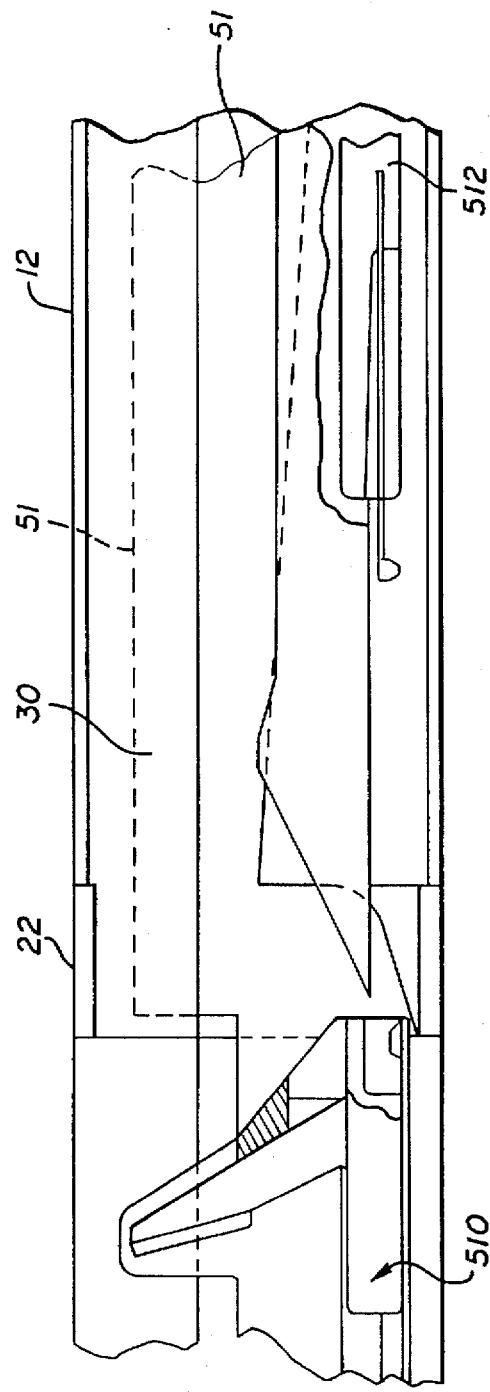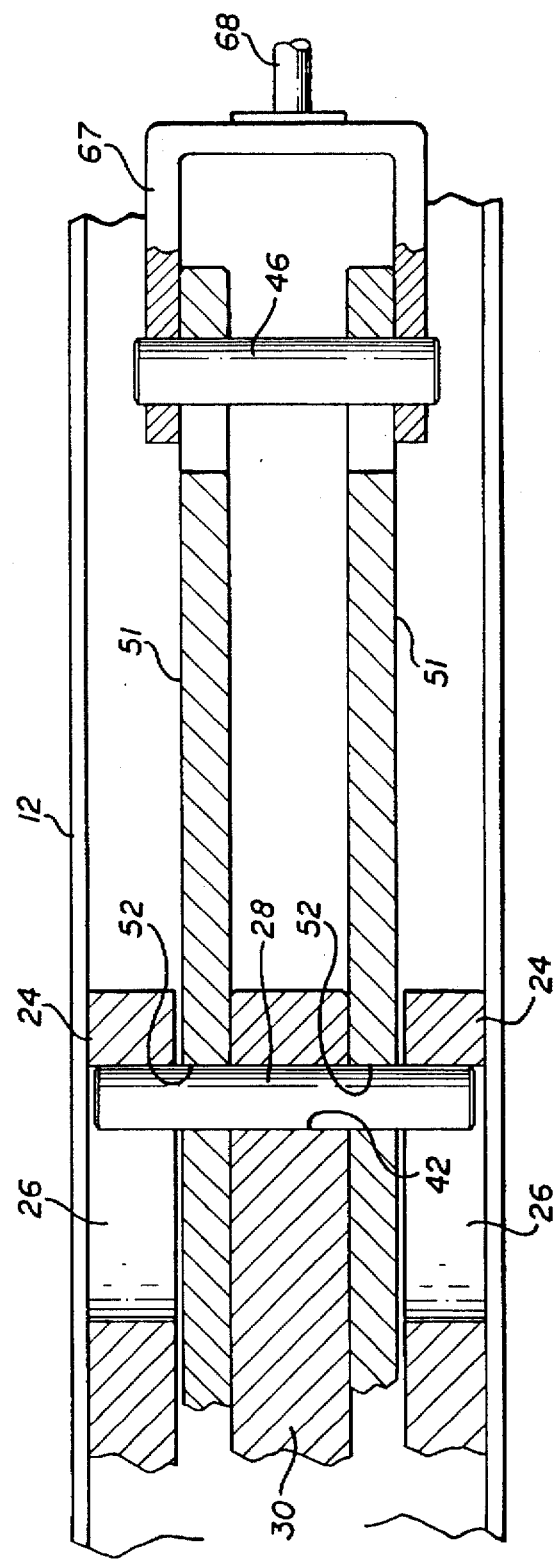

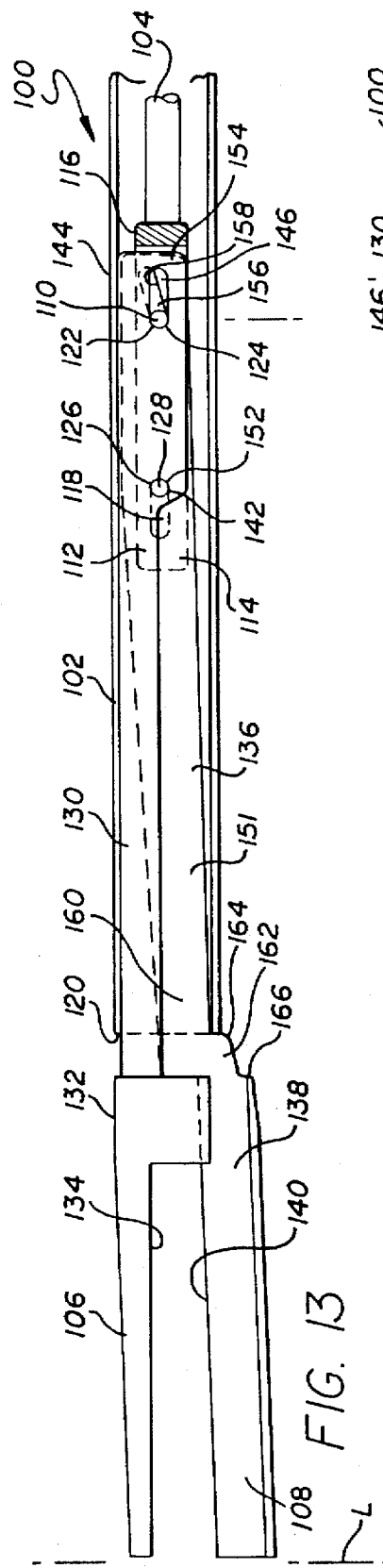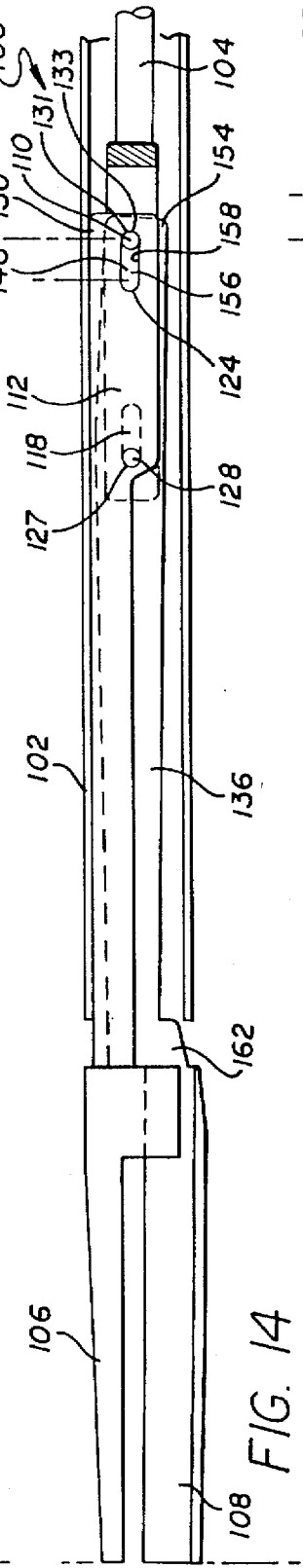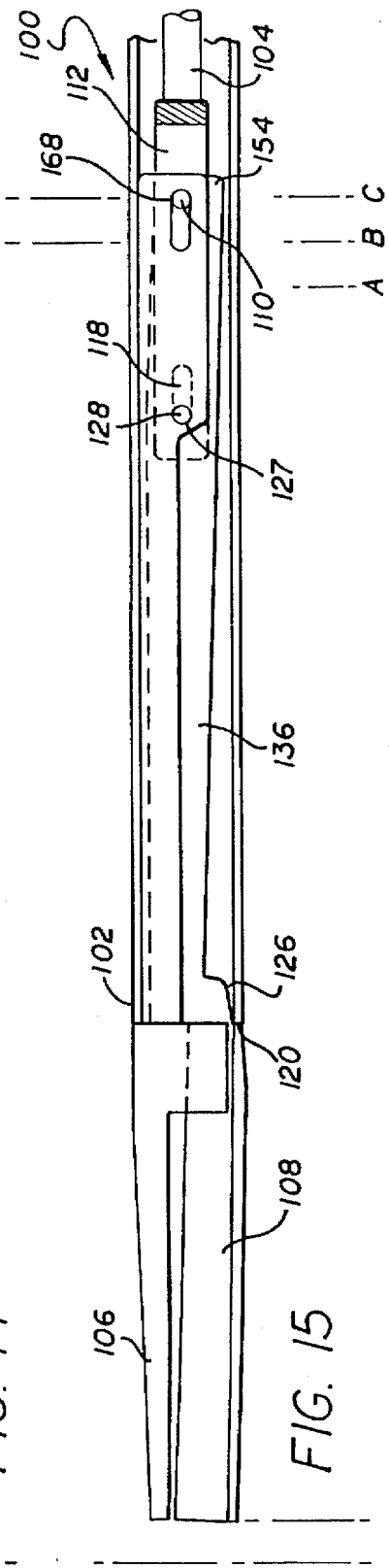

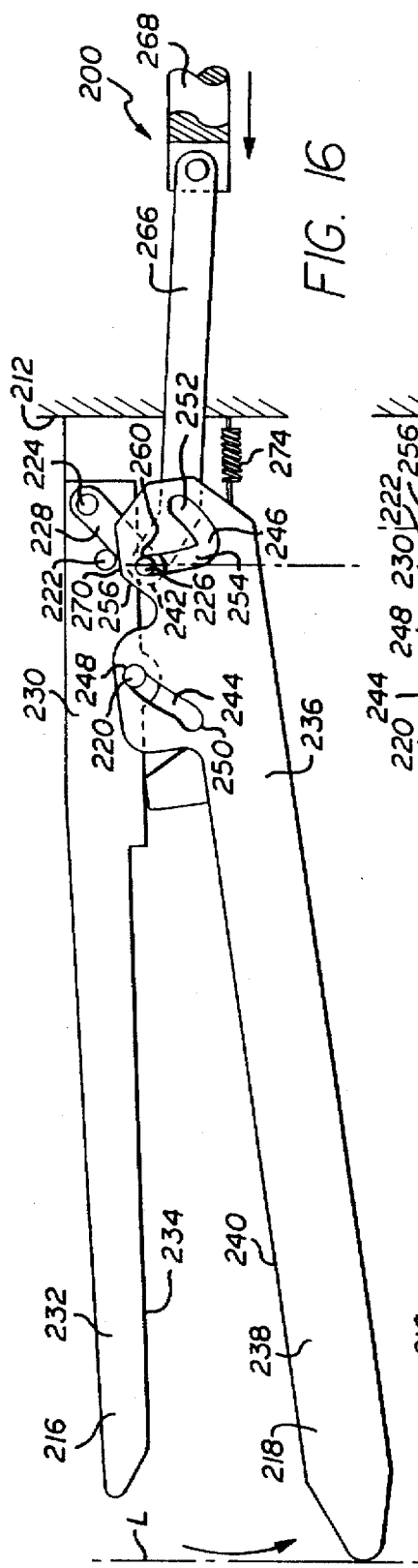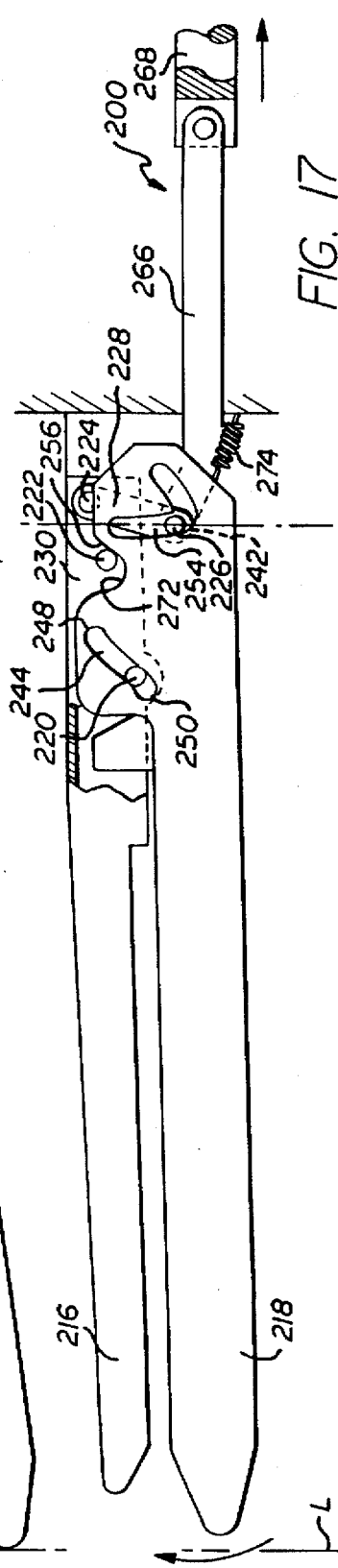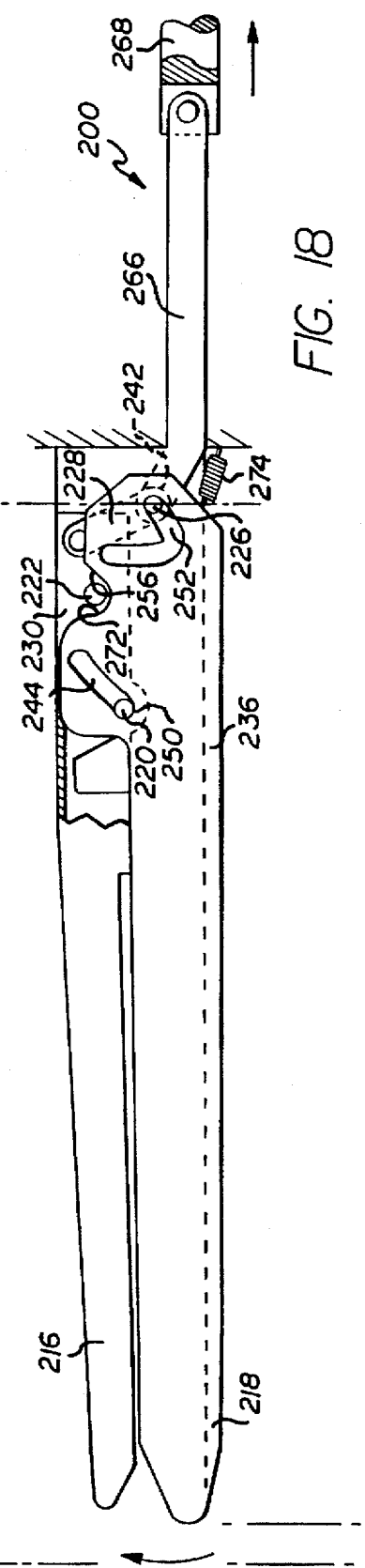

SURGICAL INSTRUMENT HAVING AN ARTICULATED JAW STRUCTURE AND A DETACHABLE KNIFE

This is a continuation of application Ser. No. 08/291,331 filed on Aug. 17, 1994, now abandoned, which is a continuation application of Ser. No. 08/055,824 filed on Apr. 30, 1993, now abandoned.

This invention relates generally to jaw-type surgical instruments and, in particular, to a jaw-type surgical instrument wherein the opposed jaws move substantially parallel over a significant part of their operating range and/or wherein one of the jaws includes a cartridge having a knife assembly that is detachable from its operating mechanism.

BACKGROUND OF THE INVENTION

A wide variety of surgical procedures used today involve surgical instrumentation having jaw structure such as grippers, graspers, dissectors, clamps, cutting elements and/or stapling elements. In each of these types of jaw structure, selected tissue is captured by the jaws for manipulation. One type of jaw structure currently used captures tissue by a pivotal action of the jaw structure wherein the jaws close progressively from a pivot point outward to the end of the jaw structure. See, for example, U.S. Pat. No. 5,040,715 to Green et al. This pivotal action, however, causes the captured tissue to be pushed away from the jaw pivot point upon approximation, possibly resulting in uneven cutting, unintentional tissue trauma, and/or inaccurate tissue measurement or joining. This type of jaw structure is also disadvantageous in endoscopic or laparoscopic procedures wherein the surgical instrument is inserted into the body through a cannula or trocar because the jaws must necessarily protrude a significant distance beyond the end of the trocar to open fully. This decreases the "maneuver room" available to a surgeon for manipulating the device within a body cavity.

A more accurate and atraumatic way of approximating surgical jaw structure is by parallel approximation. This approach has been described in European Patent Application No. 92104388.1, filed Mar. 13, 1992, wherein various camming structures are described for effecting substantially parallel movement of first and second surgical jaws. In one embodiment, a camming plate with diagonal camming slots is slidably mounted within a tubular frame. The camming plate is connected to a moveable jaw such that movement of the camming plate causes the moveable jaw to move into parallel approximation with a stationary jaw. In another embodiment, an axially slidable camming collar engages a camming surface on the moveable jaw to actuate the opening and closing of the jaws. Sliding the collar forward closes the jaws, whereas pulling the collar backward opens the jaws. This design, however, creates a very high frictional component to the overall opening and closing forces, affecting the overall ease of operation of the device. Additionally, in all of the embodiments described, the jaws are prevented from moving axially, which, as will be discussed below, precludes the user from enjoying many other advantages.

The above devices also describe jaw structures that employ a staple cartridge. Typically, the staple cartridge is provided with an axially extending slit through which a knife passes to cut the captured tissue at the time of stapling. An axially moveable actuating mechanism (e.g., a pusher rod) is used to push the knife through the cartridge. The location and structure of the knife actuating mechanism is well known for jaws having purely pivotal movement, but such is not the case for jaws that are capable of substantially parallel approximation. In this latter situation, especially in connection with endoscopic or laparoscopic procedures where accessibility is extremely limited, inclusion of the knife actuating mechanism can result in a reduction in the maximum distance the jaws can open and/or result in further penetration of the jaws beyond the end of the cannula into the body cavity to accommodate the knife actuating mechanism.

It is also desirable to have a fresh knife available after each transection. In presently available apparatus, however, the knife has been an integral part of the combined pusher rod/cartridge assembly. This design requires the pusher rod mechanism to be discarded after each use, causing waste, and requires that the overall length of the cartridge assembly be increased in size to account for the entire extended length of the pusher rod mechanism.

Another disadvantage of the above-described devices is that jaw closing is typically accomplished by actuating an axially movable rod operably connected to the jaws. Pushing on the actuating rod closes the jaws and pulling on it opens them. Using compression force on the actuating rod, however, to close the jaws around the captured tissue can result in buckling. This could have serious consequences if buckling occurred during a particularly sensitive part of the surgical procedure.

In view of the above, it should be appreciated that there is still a need for a jaw-type surgical instrument wherein the jaws are held substantially parallel over a significant part of their operating range, yet open widely with minimal extension of the jaws beyond the end of the cannula into the body cavity during the operating procedure. There is also a need for a device wherein the jaws are axially moveable to effect approximation and wherein the mechanism for closing the jaws around the captured tissue is without risk of instrument failure due to buckling of the push rod. Such a device would also preferably include an easily replaceable knife without significantly affecting the operation of the jaws or requiring frequent replacement of the knife actuating mechanism. The present invention satisfies these needs.

SUMMARY OF THE INVENTION

The present invention is embodied in a surgical instrument having an articulated jaw structure, wherein a pair of jaws are held substantially parallel over a significant part of their operating range, yet are capable of being held widely open with minimal extension of the jaws beyond the end of a mounting cannula or frame during an operating procedure. One or both jaws are adapted to be axially moveable relative to the frame. The surgical instrument also includes a jaw operating mechanism that is not subject to buckling during jaw approximation. The present invention is particularly adapted for use in surgical stapling instrumentation and permits the use of a staple cartridge/knife assembly combination that is relatively short in length and easily replaceable.

In one embodiment of the invention, the surgical instrument with articulated jaw structure includes a tubular frame and an actuating mechanism moveable inside the tubular frame. The actuating mechanism has a cam that engages corresponding camming surfaces on first and second jaws. Each of the jaws has a proximal portion defining the camming surface and a distal portion. The proximal portions of the jaws are pivotally mounted to each other. The distal portions of the jaws are configured to capture tissue between them. The cam and camming surfaces are configured such that upon movement of the cam between a first position and a second position, the jaws will pivot relative to each other between an open position and an intermediate position, respectively. One of the jaws also includes a cam stop that further engages the cam when the cam is in the second position such that upon further movement of the actuating mechanism between the second position and a third position, the jaws will retract axially into the tubular frame. One of the jaws further includes a ramp that engages a distal end of the tubular frame upon axial retraction of the jaws. The ramp is configured such that the jaws move in a substantially parallel relation between the intermediate position and an approximated position upon movement of the cam between the second position and the third position, respectively.

A feature of this embodiment of the invention is that the jaw motion may be broken down into two components, a primarily pivoting motion of the jaws during initial jaw closing, which does not consume significant axial length between the distal portions of the jaws and the tubular frame and a substantially parallel approximating motion of the jaws that does consume axial length as the jaws are retracted into the tubular frame. Through this construction, axial stroke is substantially limited to the latter high force segment of the jaw closing cycle (i.e., the compression of tissue by the approximating jaws). In turn, a shorter axial stroke means less extension of the jaws beyond the end of the tubular frame and less protrusion into the body cavity, increasing the "maneuver room" of the surgeon manipulating the instrument.

Another feature of the present invention is that the jaw mechanism may be operated by an actuating rod that closes the jaws upon pulling the rod and opens the jaws upon pushing the rod. Using tensile force to close the jaws reduces the likelihood that the actuating rod will buckle. Buckling can only occur during compressive loading, which occurs during jaw opening. Since the jaw opening force is always lower than the jaw closing force, the maximum buckling force is lower than it would be if the situation were reversed.

In a second embodiment of the present invention, the surgical instrument with articulated jaw structure includes a frame, a fixed jaw mounted to the frame at its proximal end and a moveable jaw. The moveable jaw is connected to the fixed jaw to permit movement between an open position wherein the distal ends of the jaws are spaced apart from each other and the moveable jaw is extended distally relative to the fixed jaw, and an approximated position wherein the distal ends of the jaws are closer together and the moveable jaw is substantially unextended relative to the fixed jaw. An actuating mechanism is provided for moving the jaws between the open and approximated positions.

A particular feature of the second embodiment of the invention is that the moveable jaw juts out from the fixed jaw when the jaws are open. As the jaws close, the moveable jaw moves back along the fixed jaw, pulling tissue back toward the proximal end of the jaws. This inhibits tissue from extruding out of the gap between the jaws, which is opposite to the undesirable result caused by the prior art single pivot jaws wherein the tissue is pushed out of the jaws during closing.

The present invention is also embodied in a surgical instrument having articulated jaw structure and a detachable knife. By including a mechanism for engaging and disengaging a knife, the jaws can be held substantially parallel over a significant part of their operating range, yet still open widely with minimal extension of the jaws beyond the end of their mounting cannula or frame. In addition, because the knife is detachable, the knife may be replaced often without requiring replacement of its actuating mechanism.

The surgical instrument with articulated jaw structure and detachable knife of the present invention includes a first jaw and a second jaw, one of the jaws having a longitudinal cartridge detachably mounted thereto. The first jaw and the second jaw are connected to one another to permit movement in a substantially parallel relation between an open position, which permits capture of selected tissue between the jaws and an approximated position wherein the jaws are in close proximity to and in opposed alignment with each other. A knife assembly is provided having a bearing surface, a knife blade defining a cutting edge, and a latch receiver. The longitudinal cartridge slidably receives the knife assembly such that the cutting edge of the knife blade is permitted to move longitudinally between the jaws when the jaws are in the approximated position. A knife actuating mechanism having a bearing surface and a latch is provided for moving the knife assembly from a first position at a proximal end of the cartridge to a second position located distally from the proximal end of the cartridge when the knife actuating mechanism is moved distally. The latch is received in the latch receiver of the knife assembly for moving the knife assembly back from the second position to the first position when the knife actuating mechanism is moved proximally. A further mechanism is provided for disengaging the latch when the knife actuating mechanism moves between a latched position and an unlatched position.

An advantage of the detachable knife is that the knife actuating mechanism may now be a component separate from the cartridge holding the knife assembly. In stapling instrumentation, in particular, this means that a firing mechanism for the staples no longer needs to be an integral part of the disposable staple cartridge. Because of this, the cartridge may be made smaller. This reduction in size is particularly beneficial for surgical instrumentation used in endoscopic and laparoscopic procedures.

Other features and advantages of the present invention will become apparent from the following description of the preferred embodiments, taken in conjunction with the accompanying drawings, which illustrate, by way of example, the principals of the invention.

BRIEF DESCRIPTION OF THE DRAWINGS

FIG. 2 is an assembled side view of the surgical instrument shown in FIG. 1, showing the jaws in a fully open position.

FIG. 3 is an assembled side view of the surgical instrument shown in FIG. 1, showing the jaws in an intermediate position.

FIG. 4 is an assembled side view of the surgical instrument shown in FIG. 1, showing the jaws in an approximated position, and showing a knife assembly and a knife actuating assembly made according to the present invention.

FIG. 5 is an enlarged side view of the knife assembly and the knife actuating assembly of the surgical instrument shown in FIG. 4.

FIG. 6 is a top sectional view of the surgical instrument shown in FIG. 4, taken along line 6—6.

FIG. 13 is a side view of a first modified surgical instrument having an articulated jaw structure made according to the present invention showing the jaws in a fully open position.

FIG. 14 is a side view of the surgical instrument shown in FIG. 13, showing the jaws in an intermediate position.

FIG. 15 is a side view of the surgical instrument shown in FIG. 13, showing the jaws in an approximated position.

FIG. 16 is a side view of a second modified surgical instrument having an articulated jaw structure made according to the present invention, showing the jaws in a fully open position.

FIG. 17 is a side view of the surgical instrument shown in FIG. 16, showing the jaws in an intermediate position.

FIG. 18 is a side view of the surgical instrument shown in FIG. 16, showing the jaws in an approximated position.

DETAILED DESCRIPTION OF THE PREFERRED EMBODIMENT

Figure 1:
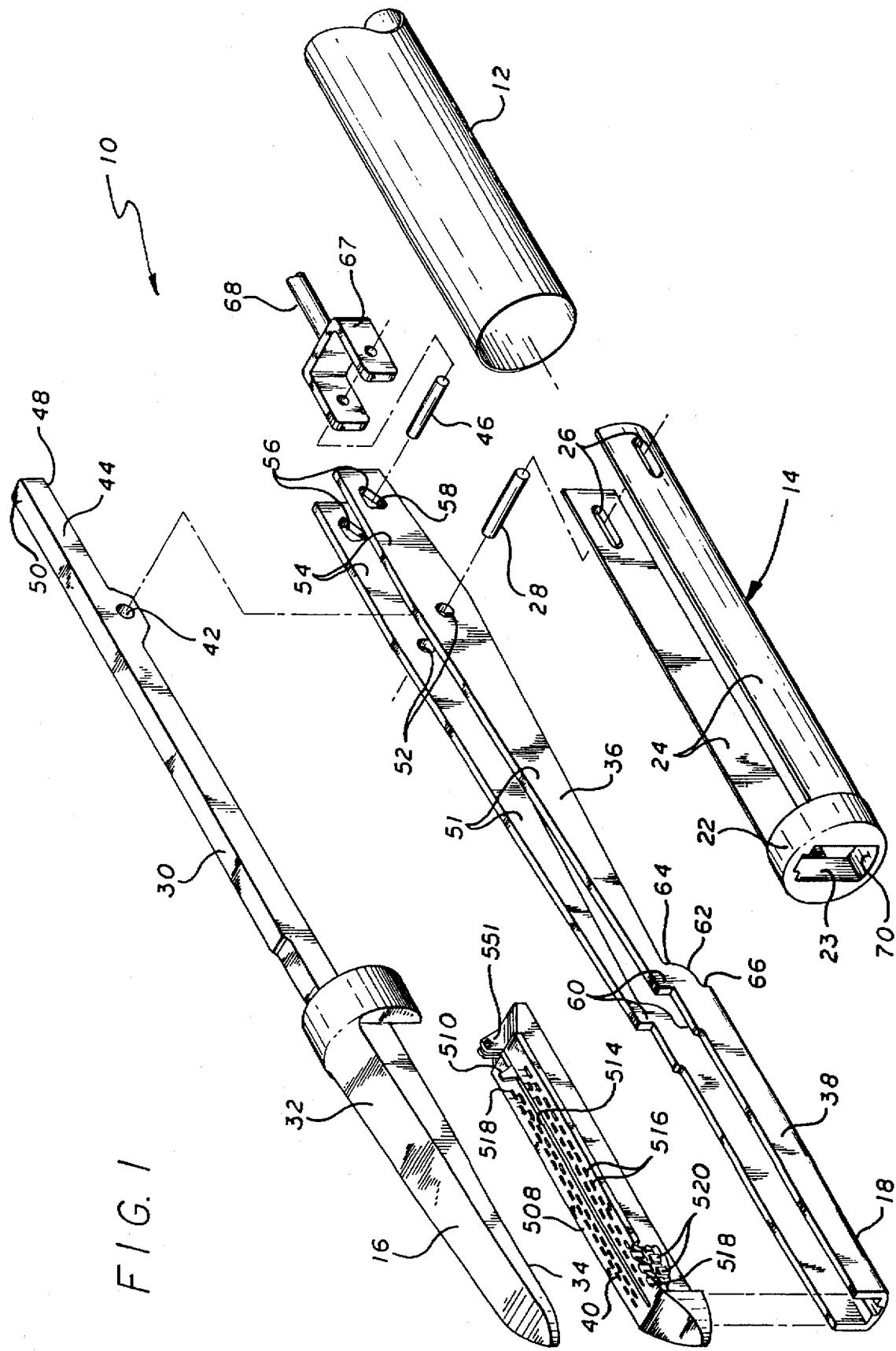
FIG. 1 is an exploded perspective view of a surgical instrument having an articulated jaw structure made according to the present invention.

A preferred surgical instrument 10 with articulated jaw structure embodying the features of the present invention is shown in pertinent part in FIGS. 1–12. Only the distal end of the instrument is shown, it being appreciated that the surgical instrument may be actuated using structure and techniques well known to those skilled in the art.

The surgical instrument 10 includes a tubular frame 12, a first or upper jaw 16 and a second or lower jaw 18. In surgical stapling apparatus, one of the jaws (in this case, the lower jaw), may include a disposable staple cartridge 508. The tubular frame preferably includes a collar 14. Both the frame and collar are preferably made of stainless steel. The collar has an end portion 22 defining an opening 23 therethrough for receiving the jaws. A pair of diametrically opposed arms 24 extend axially from the end portion into the interior of the tubular frame. Each arm defines an axially extending slot 26. A collar pin 28 is disposed and located by the slots 26 such that the collar pin extends transversely across the tubular frame. The arms of the collar form a relatively tight fit against the interior surface of the tubular frame. A proximal end (not shown) of the tubular frame is mounted to the surgical instrument by methods well known to those skilled in the art.

The upper jaw 16 has a proximal portion 30 received in the tubular frame and a distal portion 32 that extends out of the end portion 22 of the collar 14. The distal portion of the upper jaw has a tissue contacting surface 34. Similarly, the lower jaw 18 has a proximal portion 36 received in the tubular frame and a distal portion 38 that extends out of the end portion 22 of the collar 14. The upper surface of the disposable staple cartridge 508 has a tissue contacting surface 40.

The jaws are pivotally mounted to each other such that in an approximated position (FIG. 4), the tissue contacting surfaces are in opposed relationship to each other. The proximal portion 30 of the upper jaw 16 is a longitudinally extending bar that defines a transverse opening 42 for closely receiving the collar pin 28 located by the collar 14. A proximal end 44 of the upper jaw is located by a cam 46. The cam is preferably a pin that is disposed parallel to the collar pin 28, transversely across the tubular frame. The cam 46 engages a lower camming surface 48 of the proximal end of the upper jaw. The inside surface of the tubular frame engages an upper surface 50 of the proximal end of the upper jaw such that the tubular frame, the collar pin and the cam vertically locate the upper jaw.

Figure 7:
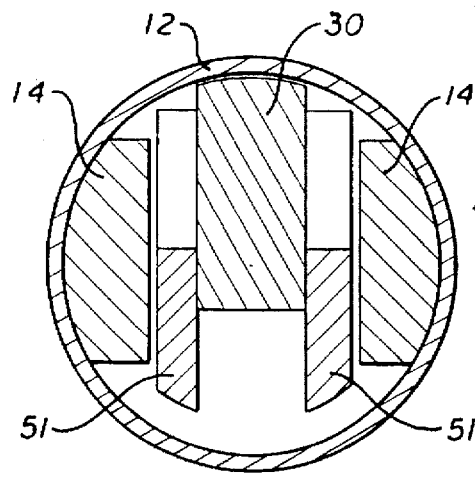
FIG. 7 is a front sectional view of the surgical instrument shown in FIG. 2, taken along line 7—7.
Figure 8:
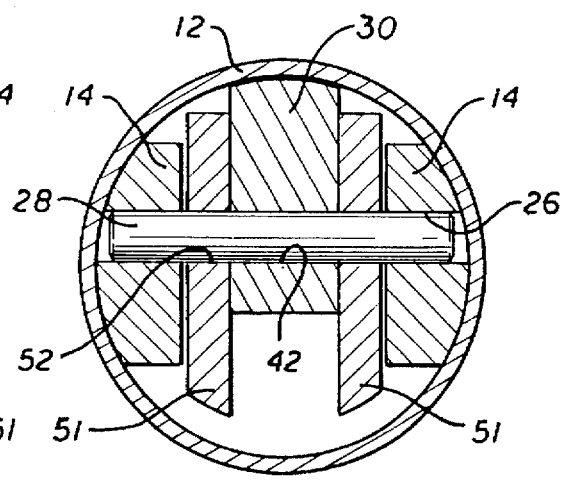
FIG. 8 is a front sectional view of the surgical instrument shown in FIG. 2, taken along line 8—8.
Figure 9:
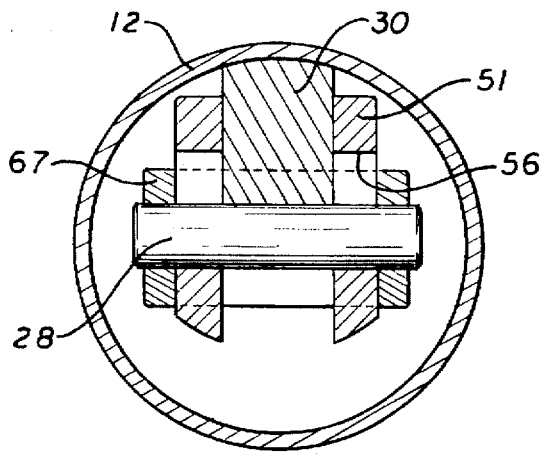
FIG. 9 is a front sectional view of the surgical instrument shown in FIG. 2, taken along line 9—9.
Figure 10:
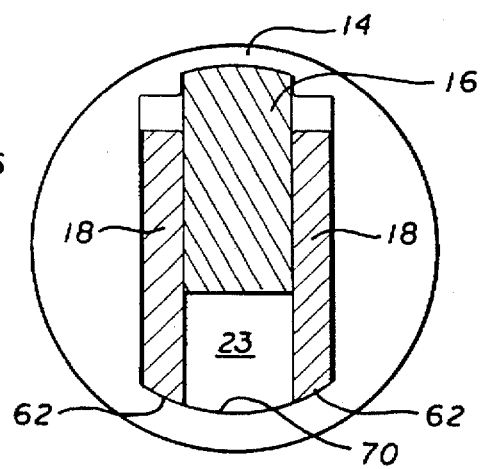
FIG. 10 is a front sectional view of the surgical instrument shown in FIG. 3, taken along line 10—10.

The proximal portion 36 of the lower jaw 18 is a pair of longitudinally extending members 51 that are located on each side, respectively, of the proximal portion 30 of the upper jaw (see FIGS. 6 and 7). Each member 51 defines a transverse opening 52 for closely receiving the collar pin 28 located by collar 14. The collar pin 28 provides an axis about which the lower jaw may pivot with respect to the upper jaw (see FIGS. 6 and 8). A proximal end 54 of each member 51 of the lower jaw defines a ramped slot 56 that receives the cam 46 (see FIGS. 1, 6 and 9). The cam engages diagonally extending camming surfaces 58 of the ramped slots. Each diagonally extending camming surface extends downwardly from the proximal end of the slot to the distal end of the slot (see FIG. 3). Each of the longitudinally extending members 51 of the lower jaw, at distal ends 60 thereof, defines a ramp 62. An upper portion 64 of each ramp is curved. Below each ramp is a shoulder 66.

The cam 46 may be fixed to a clevis 67 that is mounted to the distal end of an actuating rod 68. Preferably, the actuating rod is axially moveable within the tubular frame to move the cam between first, second and third positions to be described in more detail below. A proximal end (not shown) of the actuating rod is connected to the surgical instrument by methods known to those skilled in the art for actuation by the operator of the instrument.

With reference now to FIGS. 2–4, the operation of the jaw structure of the surgical instrument will be described. FIG. 2 shows the jaws in a fully open position with the cam 46 in a first position A. In the open position, the distal portions 32, 38 of the jaws are fully extended from the tubular member with the curved upper portion 64 of the ramp of the lower jaw adjacent to the end portion 22 of the collar 14. The collar pin 28 is in a first position at a distal end 72 of the collar arm slots 26. The cam 46 is between the lower camming surface 48 of the upper jaw and a lower end 76 of the ramped slot 56, preventing counterclockwise rotation of the lower jaw about the collar pin 28.

Figure 11:
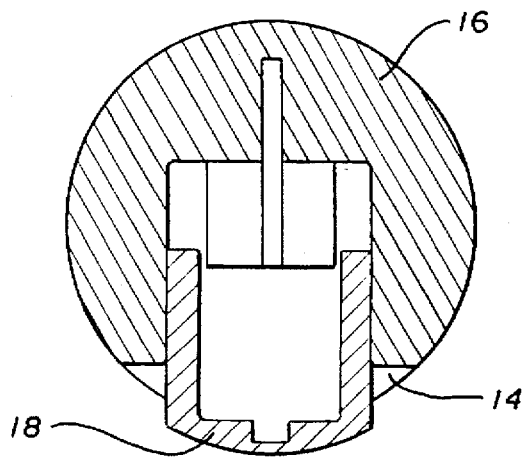
FIG. 11 is a front sectional view of the surgical instrument shown in FIG. 3, taken along line 11—11.
Figure 12:
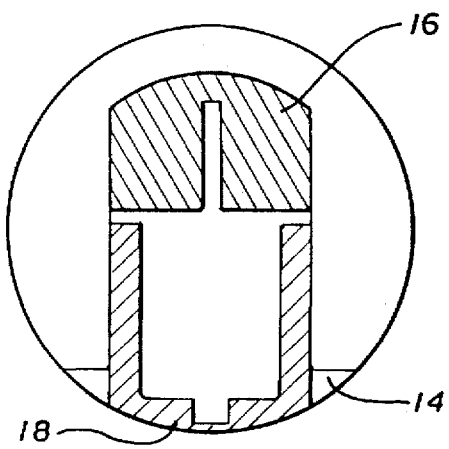
FIG. 12 is a front sectional view of the surgical instrument shown in FIG. 4, taken along line 12—12.

FIG. 3 shows the jaws in an intermediate spaced position (see also FIG. 11). By pulling on the actuating rod 68, the cam 46 is axially retracted from the first position A at the lower end 76 of the ramped slot to a second position B at an upper end 78 of the ramped slot. During the axial retraction, the cam 46 engages the diagonally extending camming surface 58 of the ramped slot to cause the lower jaw to pivot in a clockwise direction about the collar pin 28 with respect to the upper jaw. Jaw motion takes place rapidly relative to the axial movement of the actuating rod. Preferably, movement of the jaws from the fully open position to the intermediate position is accomplished with little or no axial movement of the jaws relative to the tubular member. A high clamping force between the jaws is unnecessary at this stage of the operation because the jaws are only beginning to capture tissue between their tissue contacting surfaces. Notably, in the intermediate position, the collar pin 28 is still located near the distal end 72 of the collar arm slots 26 and the cam 46 still engages the lower camming surface 48 of the upper jaw. Further, the lower jaw has moved into a position wherein further axial movement of the lower jaw will cause the curved upper portion 64 of the ramp 62 to contact a lower edge 70 of the opening 23 of the collar (see also FIGS. 1 and 10). It is the interaction between the ramp and the collar that will cause the jaws to approximate in a substantially parallel relation.

FIG. 4 shows the jaws in an approximated position wherein the cam 46 has been pulled from the second position B to a third position C. During the axial retraction, the cam 46 engages the upper end of the ramped slot 56 which acts as a cam stop 80, forcing the lower jaw and, correspondingly, the upper jaw (through the connection at the collar pin 28) to retract axially into the tubular frame. Axial retraction also causes the jaws to approximate due to engagement of the ramp 62 with the lower edge 70 of the opening of the collar (see also FIG. 12).

During the approximating phase of operation, jaw movement takes place slowly in relation to actuating rod movement. High clamping forces are desired at this point due to the high force required to compress the tissue captured between the jaws. High force multiplication occurs as the ramp 62 bears against the lower edge of the opening of the collar 14. Notably, in the approximated position, the collar pin 28 has moved to a proximal end 82 of the collar arm slots 26 and the jaws are fully retracted into the collar, with the collar contacting the shoulder 66 on the lower jaw adjacent the lower end of the ramp 62.

It will be appreciated that the above described construction enables the jaws of the instrument to open widely with relatively little extension of the jaws beyond the end portion 22 of the collar 14 (as shown by the vertically oriented dashed line L at the left end of FIGS. 2-4). This result is achieved by dividing the jaw closure action into two parts: a first part, wherein the actuating rod moves the cam from position A to position B, which requires very little, if any, axial movement of the jaws and, a second part, wherein the actuating rod moves the cam from position B to position C, which does require axial movement of the jaws. Notably, the second part of the jaw closure action is limited to the segment where high forces are required to compress the captured tissue between the jaws. It will also be appreciated that the jaws are held substantially parallel over a significant portion of their operating range, and, in particular, between their intermediate and approximated positions.

In the preferred embodiment, the ramped slots 56 of the lower jaw have a triangular or a quadrilateral shape. This permits the lower jaw to move vertically or to rotate relative to the cam 46, without requiring actuation of the actuating rod by the operator.

With reference now to FIGS. 13-15, a first modified embodiment 100 of the surgical instrument is shown having a tubular frame 102, an actuating rod 104, an upper jaw 106 and a lower jaw 108. In this embodiment, the collar has been omitted and an elongated clevis 112 has been fixed to the distal end of the actuating rod 104. The clevis has a distal portion 114 and a proximal portion 116. The distal portion 114 defines an axially extending slot 118 for locating a clevis pin 128 such that the clevis pin extends transversely across the tubular frame 102. A cam 110, in the form of a pin, is fixably mounted to the proximal portion 116 of the clevis such that it is disposed parallel to the clevis pin 128 and transversely across the tubular frame.

The upper jaw 106 has a proximal portion 130 received in the tubular frame 102 and a distal portion 132 that extends out of a distal end 120 of the tubular frame. The distal portion of the upper jaw has a tissue contacting surface 134. Similarly, the lower jaw 108 has a proximal portion 136 received in the tubular frame and a distal portion 138 that extends out from the distal end of the tubular frame. The distal portion of the lower jaw has a tissue contacting surface 140.

The jaws are pivotally mounted to each other such that in an approximated position (FIG. 15), the tissue contacting surfaces are in opposed relationship to each other. The proximal portion 130 of the upper jaw 106 is a longitudinally extending bar that defines a traverse opening 142 for closely receiving the clevis pin 128. A proximal end 144 of the upper jaw defines an axially extending slot 146 that receives the cam 110. The slot 146 is horizontally disposed in FIGS. 13-15.

The proximal portion 136 of the lower jaw 108 is a pair of longitudinally extending members 151 that are located on each side, respectively, of the proximal portion 130 of the upper jaw. Each longitudinally extending member 151 defines a transverse opening 152 for closely receiving the clevis pin 128. The clevis pin 128 provides an axis about which the lower jaw may pivot with respect to the upper jaw. A proximal end 154 of each member 151 of the lower jaw defines a ramped slot 156 that receives the cam 110. The cam engages camming surfaces 158 of the ramp slots. In FIG. 13, the camming surface extends downwardly from the proximal end of the slot to the distal end of the slot. Each of the members 151 of the lower jaw also defines a ramp 162 at a distal end 160 thereof. An upper portion 164 of each ramp is curved. Below each ramp is a shoulder 166.

FIG. 13 shows the jaws in a fully open position with the cam 110 in a first position A and the distal portions 132, 138 of the jaws fully extended from end 120 of the tubular frame 102. The cam 110 is at a distal end 122 of the upper jaw slot 146 and at a distal end 124 of the ramped slot of the lower law 156, preventing counterclockwise rotation of the lower jaw about the clevis pin 128. The clevis pin 128 is in a first position at a proximal end 126 of the clevis slot 118. Upper surfaces on the proximal portions of both jaws may be configured to contact the interior surface of the tubular frame.

FIG. 14 shows the jaws in an intermediate spaced position wherein the cam 110 has been pulled from the first position A at the distal end 124 of the ramped slot 156 of the lower jaw to a second position B at a proximal end 131 of the ramped slot. During the axially retraction, the cam 110 engages the camming surface 158 of the ramped slot to cause the lower jaw to pivot about the clevis pin 128 in a clockwise direction with respect to the upper jaw. Notably, in the intermediate position, the clevis pin 128 is now located at a distal end 127 of the clevis slot 118 and the cam 110 is located at a proximal end 133 of the upper jaw slot 146, it being appreciated that the upper and lower jaw slots are now horizontally aligned.

FIG. 15 shows the jaws in an approximated position wherein the cam 110 has been pulled from the second position B to the third position C. During the axial retraction, the cam engages both slot ends of the upper and lower jaw slots, the slot ends acting as a cam stop 168, forcing the jaws to retract axially into the tubular frame. Axial retraction further causes the jaws to approximate due to engagement of the ramp 162 with the end 120 of the tubular frame. The lower jaw may also be permitted to rotate about the cam 110 during retraction. Notably, in the approximated position, the clevis pin 128 is still located at the distal end 127 of the clevis slot 118. It will be appreciated that the operation and benefits of the present embodiment are generally similar to that of the previously described embodiment.

With reference now to FIGS. 16–18, a second modified embodiment 200 of the present invention is shown wherein only one of the jaws is axially movable. The surgical instrument includes a frame member 212, an upper jaw 216 and a U-shaped lower jaw 218. The upper jaw has a proximal portion 230 fixably mounted to the frame member and a distal portion 232 having a tissue contacting surface 234. The lower jaw 218 has a proximal portion 236 mounted to the upper jaw and a distal portion 238 having a tissue contacting surface 240. The jaws are pivotally mounted to each other such that in an approximated position (FIG. 18), the tissue contacting surfaces of the jaws are in opposed relationship to each other.

The proximal portion 230 of the upper jaw includes an articulating mechanism for opening and closing the jaws. In particular, the proximal portion defines three pins arranged parallel to each other and which protrude transversely from each side of the upper jaw, a first pin 220, a cam pin 222 and a pivot pin 224. A link 228 is pivotally mounted to the pivot pin 224 on each side of the upper jaw. As the link on each side of the jaw is identical, only one will be described. A distal end 242 of the link is provided with a link pin 226 that is parallel to the other pins and extends outwardly from the link. It will be appreciated that there is a space between the links for receiving a knife actuating assembly, as more fully described in connection with FIG. 19.

The proximal portion 236 of the lower jaw has an articulating mechanism that corresponds to the articulating mechanism of the upper jaw. In the preferred embodiment, both upstanding walls of the U-shaped lower jaw have identical corresponding articulating structure at the proximal portions, namely, a first slot 244 for receiving the first pin 220 of the upper jaw and a second slot 246 for receiving the link pin 226 located at the distal end of the link 228. The first slot 244 extends diagonally downward from a proximal end 248 to a distal end 250. The second slot 246 has two portions, a proximal portion 252 having a mild slope relative to the longitudinal axis of the lower jaw and a distal portion 254 having a steep slope that is preferably disposed at an angle greater than 90° relative to the longitudinal axis of the lower jaw. The proximal portion of the lower jaw further includes a cam surface 256 for engaging the cam pin 222 of the upper jaw. The cam surface extends diagonally upward towards the proximal end of the lower jaw.

The distal ends of the links 228 may be mounted to a clevis 266 of an actuating rod 268 which is axially movable. Preferably, the clevis is pivotally mounted to the actuating rod about a traverse axis parallel to the pins 220, 222, 224, 226. A proximal end (not shown) of the actuating rod is connected to the surgical instrument by methods known to those skilled in the art for actuation by the operator of the instrument. The link pin 226 is movable between first, second and third positions to be described below in more detail.

The operation of the jaw structure of the second modified embodiment will now be described. FIG. 16 shows the jaws in a fully open position with the link pin 226 in a first position A and the lower jaw extended distally relative to the upper jaw. The first pin 220 is in a first position at the proximal end 248 of the first slot 244 whereas the link pin 226 is at an upper end 260 of the distal portion 254 of the second slot. The cam pin 222 is at an upper end 270 of the cam surface 256.

FIG. 17 shows the jaws in an intermediate spaced position wherein the link pin 226 has been pulled by the actuating rod from the first position A to a second position B. During the axial retraction, the link 228 rotates in a counterclockwise direction causing the link pin 226 to ride down the distal portion 254 of the second slot, pulling the lower jaw proximally. It is this axial linear motion of the lower jaw that pulls tissue into the gap between the jaws and inhibits tissue from extruding out of the gap during approximation. In addition to the axial motion, the lower jaw also draws closer to the upper jaw due to its rotation about the link pin 226 as the first pin 220 slides from a first position at the proximal end 248 of the first slot to a second position near the distal end 250 of the first slot. Jaw motion from the open position to the intermediate position, takes place rapidly relative to actuating rod movement. A high clamping force is unnecessary at this stage of the operation because the jaws are only beginning to capture tissue. Notably, in the intermediate position, the cam pin 222 is at a lower end 272 of the cam surface 256.

FIG. 18 shows the jaws in an approximated position wherein the link pin 226 has been pulled by the actuating rod from the second position B to a third position C. During the axial retraction, the link pin 226 rides up the proximal portion 252 of the second slot, causing the lower jaw to close further as it rotates about the first pin 220. During this phase of the operation, jaw motion takes place slowly in relation to actuating rod movement. High clamping force is desired due to the high force required to compress the captured tissue between the jaws. Notably, in the approximated position, the first pin 220 moves to the distal end 250 of the first slot and the cam pin 222 remains at the lower end 272 of the cam surface 256.

It will be appreciated that the cam pin 222 is particularly useful for reopening the jaw structure. In moving from the approximated position to the intermediate position, the cam pin 222 will engage the cam surface 256 to urge the lower jaw to its fully open, extended position. On the other hand, a biasing mechanism, such as a spring 274, may be connected between the proximal portion 236 of the lower jaw and the frame 212 to urge the lower jaw from its fully open position to the intermediate position (see FIG. 16).

As with the previously described embodiments, the second modified embodiment enables the jaws of the instrument to open widely with relatively little extension of the jaws beyond the end of the frame. Furthermore, the jaws are held substantially parallel over a significant portion of their opening range and, in particular, between their intermediate and approximated positions.

Figure 20:
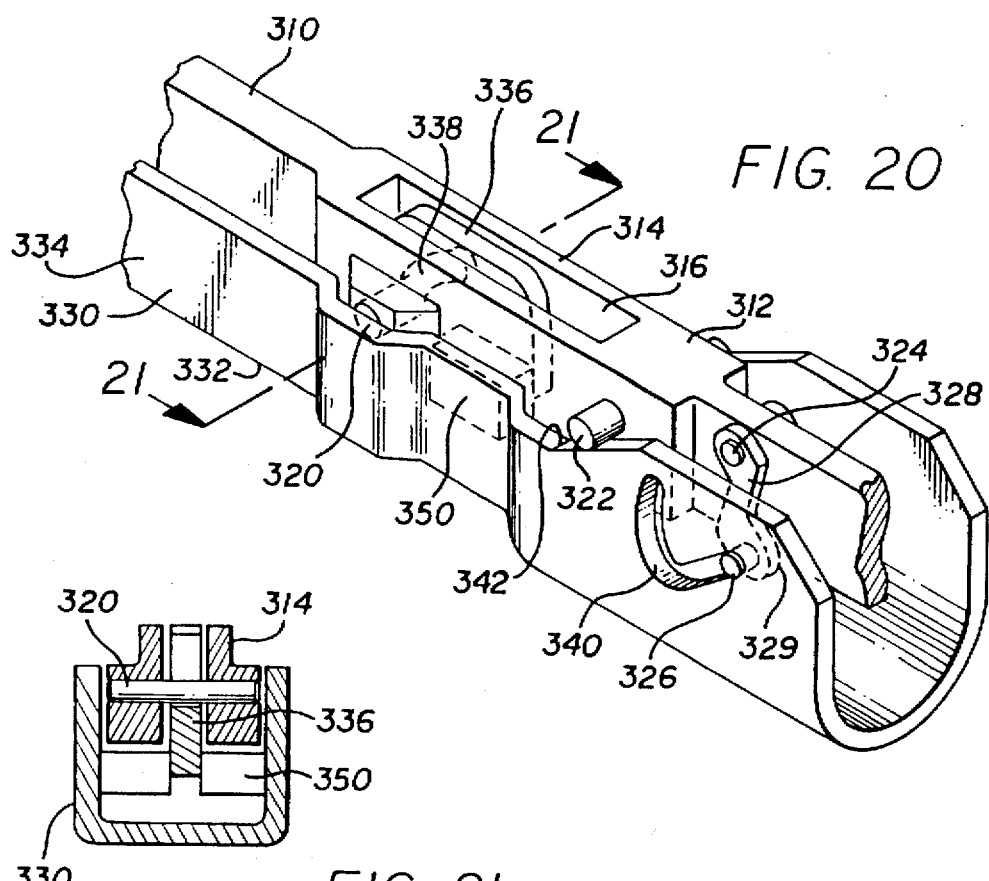
FIG. 20 is a partial perspective view of a third modified surgical instrument having an articulated jaw structure made according to the present invention.
Figure 21:
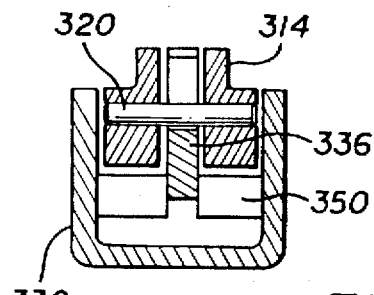
FIG. 21 is a rear sectional view of the surgical instrument shown in FIG. 20 taken along line 21—21.

With reference to FIGS. 20 and 21, a third modified embodiment of the present invention is shown. As with the second modified embodiment, an upper jaw 310 has a proximal portion 312 that includes an articulating mechanism for operating the jaws. The proximal portion includes a collar 314 defining a longitudinally extending opening 316 at the center thereof. A first pin 320 is mounted to the collar transversely across the longitudinally extending opening 316. A cam pin 322, parallel to the first pin 320, extends outwardly from each side of the collar. A pivot pin 324, parallel to the first pin and the cam pin, extends outwardly from each side of the proximal portion of the upper jaw, adjacent the collar. A link 328 is pivotally mounted to each side of the upper jaw at the pivot pin 324. A distal end 329 of each link is provided with a link pin 326 that is parallel to the other pins and extends outwardly from its respective link.

A U-shaped lower jaw 330 includes a base wall 332 and two upwardly extending side walls 334. In addition, the lower jaw is provided with an interior cam plate 336 that is disposed in the longitudinally extending opening 316 of the upper jaw. A mounting block or blocks 350 may be used to mount the cam plate 336 to the upwardly extending side wall(s) of the lower jaw. The mounting blocks may be placed between the sides of the cam plate and each of the upwardly extending walls, just below the lower surface of the upper jaw. As in the second modified embodiment, a first slot 338 is provided for engaging the first pin 320, a second slot 340 is provided for engaging the link pin 326 and a cam surface 342 is provided for engaging the cam pin 322. In this instance, however, the first slot 338 is disposed in the interior cam plate 336 of the lower jaw, not in the upwardly extending walls. In this regard, it will appreciated that the operation of the jaws of the third embodiment, between the fully opened, the intermediate and the approximated positions is similar to that fully described in connection with the second modified embodiment and need not be further described.

Figure 27:
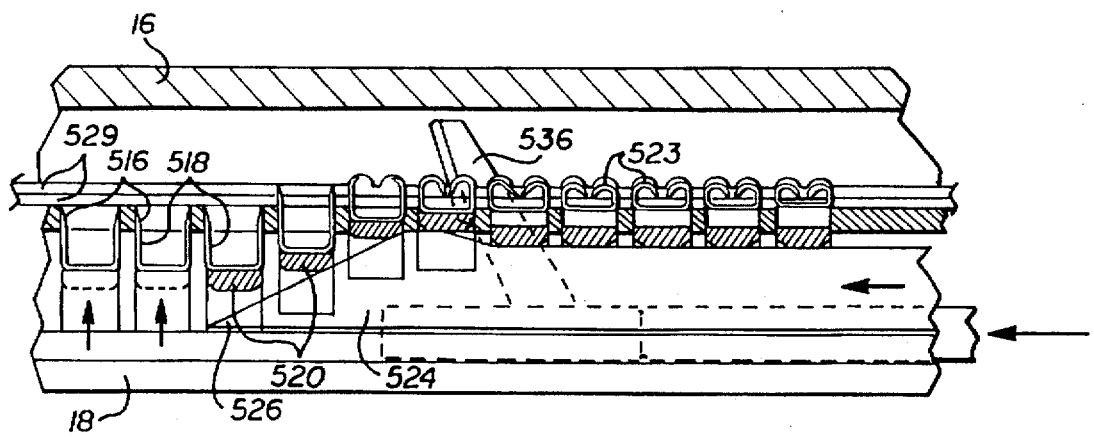
FIG. 27 is a side sectional view of a surgical stapler, showing the stapling and cutting of tissue between the jaws of the stapler.

With reference now to FIGS. 1 and 4, the surgical instrument, in this case, a surgical stapling apparatus, is shown having a knife assembly 510 mounted in the disposable staple cartridge 508 for longitudinally slidable movement therein. The construction of the staple cartridge and the techniques for operating the stapling mechanism are well known to those skilled in the art. Briefly, however, the staple cartridge is typically a longitudinally extending member that is detachably mounted within the U-shaped lower jaw 18 of the surgical instrument. The staple cartridge includes a longitudinal slit 514 and a number of slots 516 arranged on both sides of the slit and adapted to accommodate staples 518 and staple pushers 520 (see also FIG. 27). The upper jaw or anvil jaw 16 of the surgical stapler typically includes a longitudinal slit (not shown) aligned with the slit 514 of the staple cartridge when the jaws are in the approximated position and also includes a plurality of rows of depressions 523 aligned with the staple slots 516 for bending the staples fired from the staple cartridge. To eject the staples, a plurality of pusher rods 524, pointed at their distal ends 526 are inserted through additional slits 528 in the proximal end of the staple cartridge (see FIGS. 23 and 24) to slide longitudinally therein. The pusher rods contact the pushers 520, causing the pushers to rise and expelling the staples 518 out of their slots (FIG. 27). Tissue 529 captured between the jaws is thus stapled and cut.

Figure 26:
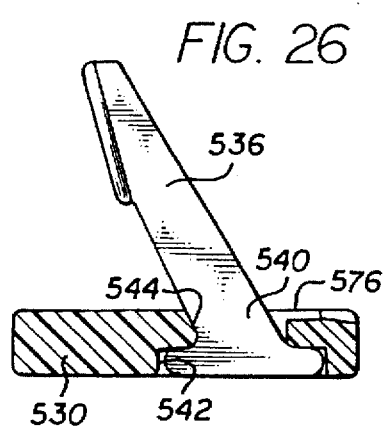
FIG. 26 is an enlarged sectional view of the knife assembly.

With reference now to FIGS. 22A-H, the knife assembly 510 is shown mounted in the staple cartridge. The knife assembly includes a longitudinally extending knife support 530 having a proximal end 532 and a distal end 534 and a knife blade 536 defining a cutting edge 538. The knife blade extends upwardly from the support with its cutting edge facing distally. With reference to FIG. 26, the knife blade includes an integral base 540 that may be seated in a notched area 542 at the bottom of the knife support with the cutting edge of the blade protruding through an opening 544 at the top of the knife support.

The proximal end 532 of the knife support includes a pair of latch receivers 546 extending transversely from each side of the knife support. Each latch receiver may be configured as a trapezoid having a proximally located, upwardly extending, ramp 548 and a distally located, downwardly extending, ramp 550.

Figure 24:
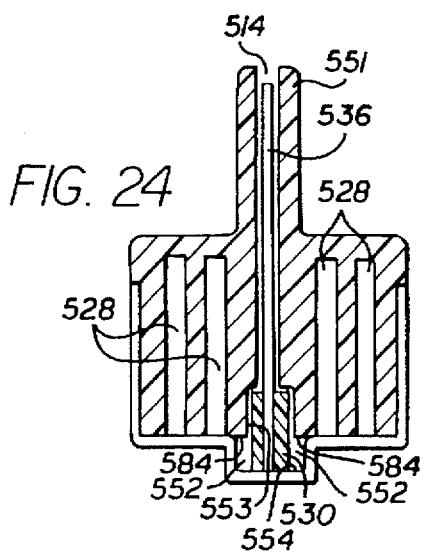
FIG. 24 is a sectional view taken along line 24—24 in FIG. 22C.

The knife assembly is received in a longitudinally extending opening of the staple cartridge, with the knife blade extending upwardly through the longitudinal slit 514 of the staple cartridge. The knife blade is initially disposed in a protective shield 551 at the proximal end of the staple cartridge. The bottom of the staple cartridge includes a recessed portion 553 and a trough portion 554 for receiving the knife support 530 of the knife assembly (See FIG. 24). The recessed portion 553 closely receives the knife support, whereas the trough portion 554 defines a tunnel 552 on each side of the knife support, the purpose of which will be described in more detail below in connection with the operation of the knife actuating assembly. The additional slits 528 shown in FIG. 24 are for receiving the pusher rods 524 previously described.

A knife actuating assembly 512 for moving the knife is also shown in FIGS. 22A-H. The knife actuating assembly includes a base 556, a blade support 558 and two latch assemblies 560. The blade support is preferably a metal blade that is fixedly centered on the top of the base and disposed in a longitudinal direction. The latch assemblies each include a flexible latch arm 562 having a proximal end 564 and a distal end 566. A latch 568 is disposed at the distal end of each latch arm. The proximal ends of the latch arms are fixedly mounted within a recess 570 at the bottom of the base. The recess includes a beveled portion 572 at the distal end of the base to permit the latch arms to deflect upwardly. The proximal end (not shown) of the knife actuating assembly is connected to the surgical instrument by methods known to those skilled in the art for actuation by the operator of the instrument. The knife actuating assembly is movable between a first latched position, a second latched and an unlatched position, as will be described in more detail below.

Preferably, the pusher rods 524 are also mounted to the knife actuating assembly to ensure that the pusher rods and the knife blade 536 move simultaneously in a predetermined manner through the staple cartridge during the stapling/cutting procedure. With reference to FIGS. 4 and 5, the knife assembly 510 and the knife actuating assembly 512 are shown located in the first embodiment of the invention. The staple cartridge and knife assembly 510 form an integral disposable part that is located in the distal portion of the lower jaw (see FIG.1). The knife actuating assembly is located in the tubular frame 12 between the longitudinally extending members 51 of the lower jaw. The blade support 558 and pusher rods 524 are located below the proximal portion 30 of the upper jaw. Alternatively, the proximal portion of the upper jaw may be configured to permit free movement of the blade support and pusher rods longitudinally through the tubular frame. Notably, when the jaws are in the fully open and intermediate positions, the knife assembly typically cannot be operated because it is out of alignment with the knife actuating assembly. In the approximated position (FIGS. 4 and 5), the knife assembly and knife actuating assembly are aligned. In this position, the staple cartridge is ready to be fired and the knife is ready to be actuated to cut through tissue captured between the jaws.

Figure 19:
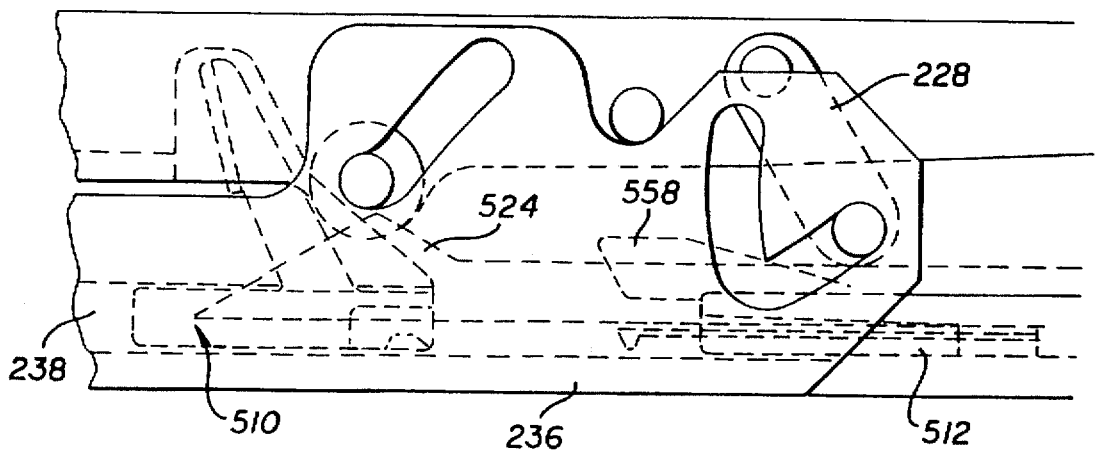
FIG. 19 is an enlarged side view of a portion of the surgical instrument shown in FIG. 18, and showing a knife assembly and a knife actuating assembly made according to the present invention.

With reference to FIG. 19, the second modified embodiment is similarly shown having the knife assembly 510 and knife actuating assembly 512 located in the surgical instrument. The knife assembly is located in the distal portion 238 of the lower jaw and the knife actuating assembly is located at the bottom of the proximal portion 236 of the lower jaw between the links 228. The blade support 558 and pusher rods 524 are located below the proximal portion 230 of the upper jaw. As with the first embodiment shown in FIG. 5, the knife assembly typically cannot be operated when the jaws are in the open and intermediate positions (FIGS. 16 and 17), but is operable in the approximated position (FIG. 18).

Figure 23:
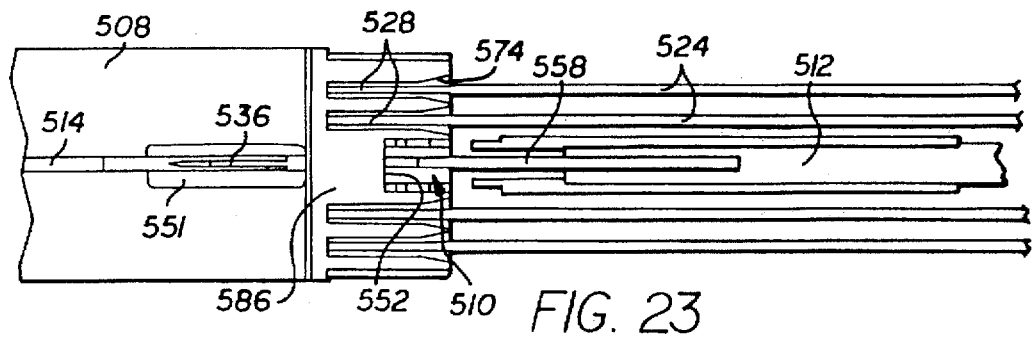
FIG. 23 is a top view of the knife assembly and the knife actuating assembly shown in FIG. 22A.

With reference now to FIG. 23, the knife actuating assembly 512 is shown initially engaged to the knife assembly 510 and staple cartridge 508. In particular, the pusher rods 524 are located by the slits 528, which have beveled outer edges 574 to facilitate entry. The blade support 558 is located by a shallow slit 576 formed into the upper surface of the knife support 530 (See also FIGS. 24 and 26). The shallow slit may also be beveled to facility entry of the blade support.

Figure 22A:
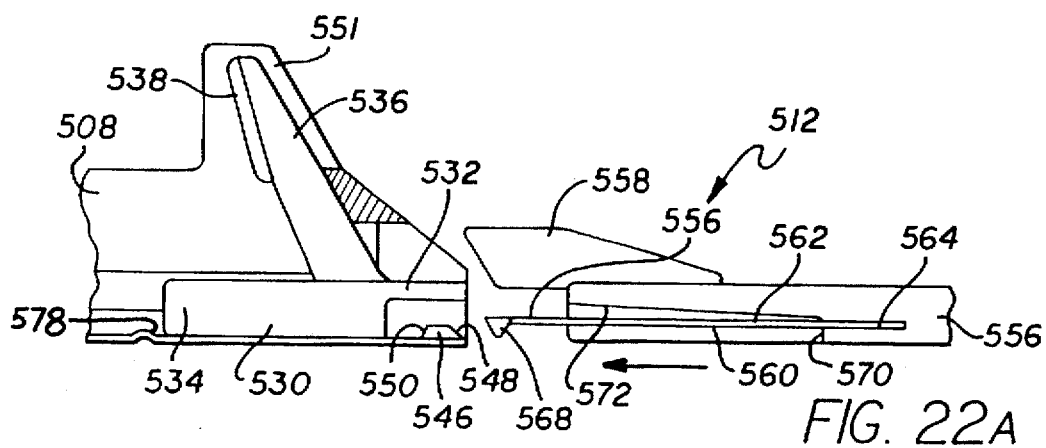
FIGS. 22A-H are enlarged sectional views of a knife assembly and a knife actuating assembly made according to the present invention, wherein the assemblies are shown at various stages of operation in a surgical instrument.
Figure 22B:
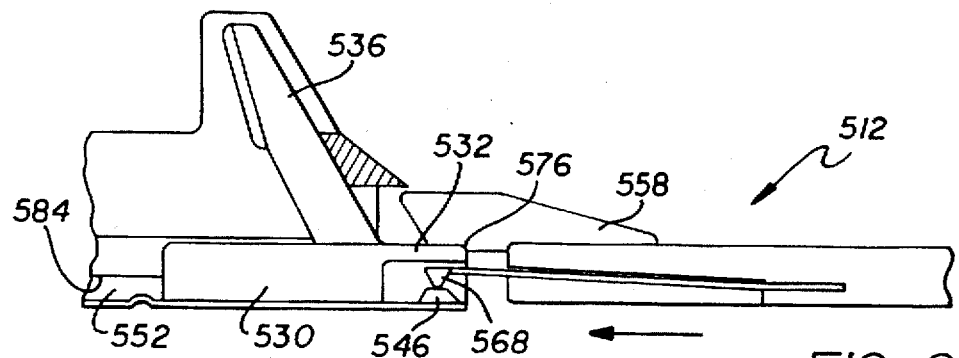
Figure 22C:
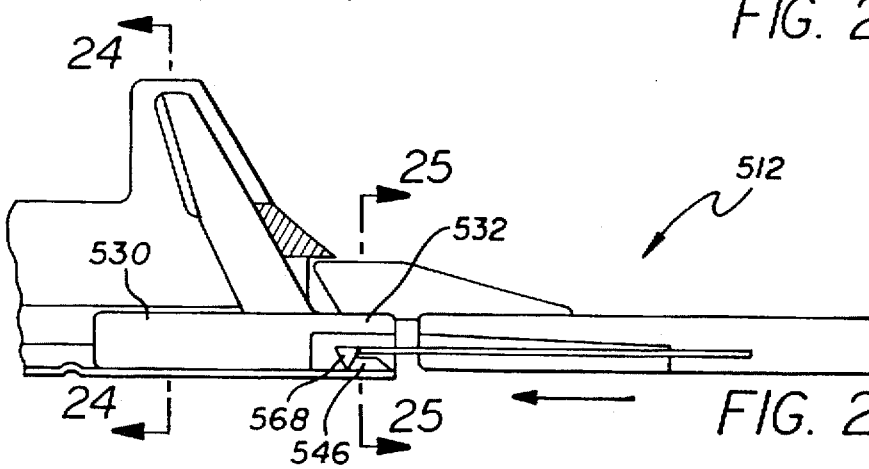
Figure 25:
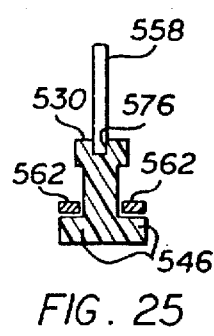
FIG. 25 is a sectional view taken along line 25—25 in FIG. 22C.

With reference now to FIGS. 22A–22H the operation of the knife actuating assembly will be described. FIG. 22A shows the knife actuating assembly in an unlatched position wherein the latch 568 and the blade support 558 are out of contact with the staple cartridge 508 and knife assembly 510. FIG. 22B shows a prelatched position, with the knife actuating assembly moved from right to left as shown by the arrow. The blade support 558 is located in the shallow slit 576 at the top of the knife support 530 and the latch receiver 546 has deflected the latch 568 upwardly as the latch rides up the ramp 548. Notably, the knife assembly has not moved forward yet, despite the horizontal component of force applied by the latch to the latch receiver, because a detent 578 integral with the bottom of the cartridge offers adequate resistance to forward motion at this point. FIG. 22C shows a first latched position at the proximal end of the cartridge, wherein the latch has dropped behind the latch receiver (see also FIG. 25 showing the latch arms 562 disposed over the latch receivers 546).

Figure 22D:
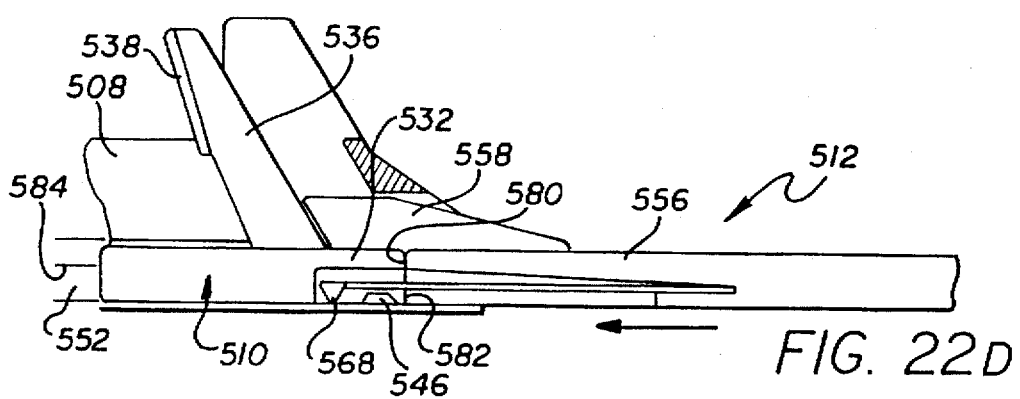

FIG. 22D shows the knife actuating assembly in a firing position, wherein a bearing surface 580 of the base 556 contacts a bearing surface 582 at the proximal end 532 of the knife assembly and starts pushing the knife assembly forward, overcoming the resistance of the detent. Notably, the blade support 558 does not quite contact the back surface of the knife blade 536, its purpose being to act as a support in case the resistance to cutting is so great that the knife assembly tends to tilt backwards. It should also be appreciated, that the latches 568 of the knife actuating assembly are engaged in the tunnels 552 located on each side of the knife support 530 of the knife assembly, at the bottom of the cartridge (see FIG. 24). The location of the latches in the tunnels becomes important when it is time to withdraw the knife, because a roof 584 of each tunnel will ensure that the latches cannot disengage from the latch receivers until the knife is fully retracted.

Figure 22E:
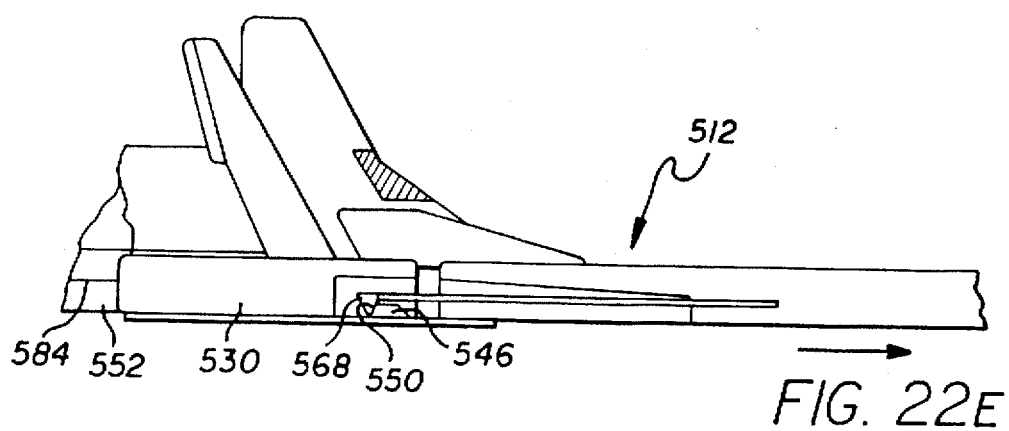
Figure 22F:
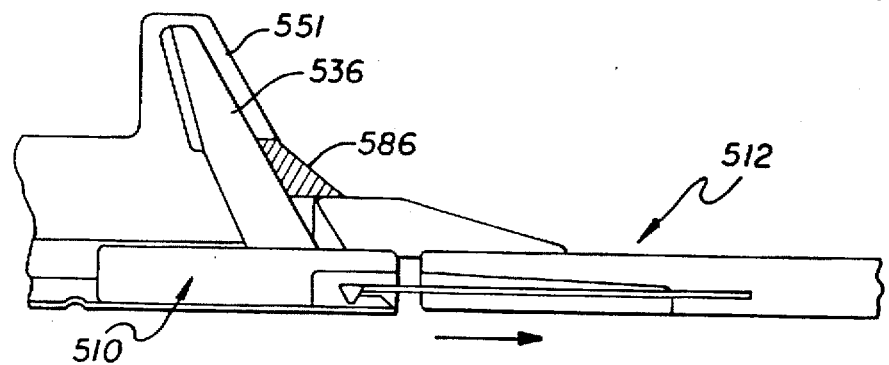
Figure 22G:
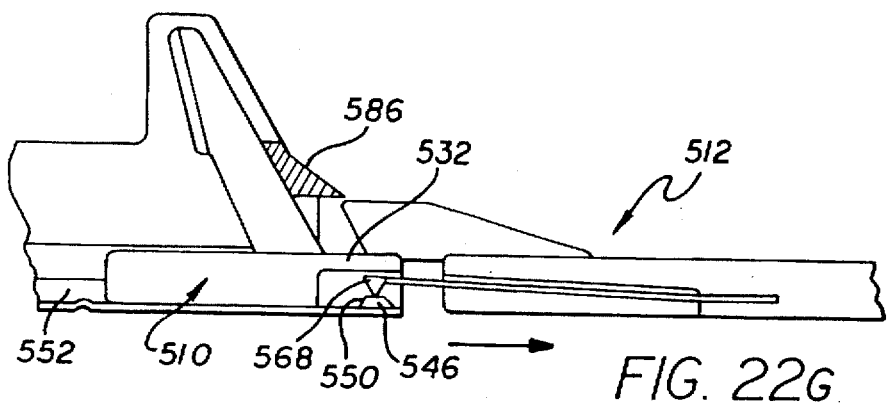
Figure 22H:
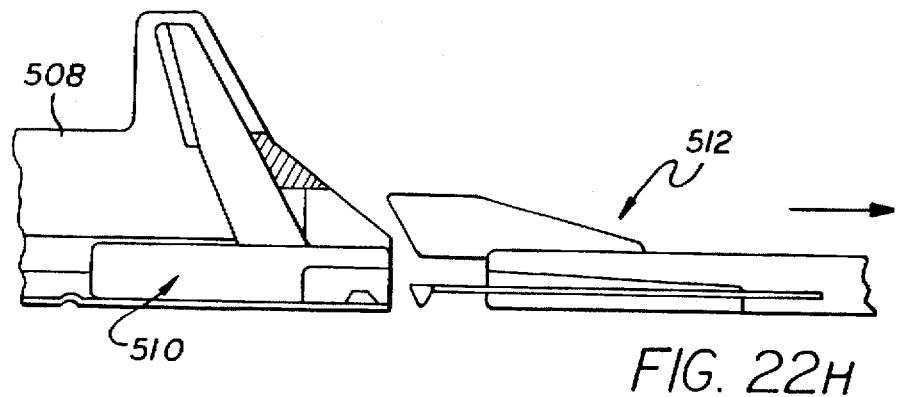

FIG. 22E shows the knife assembly in a second latched position wherein the knife actuating assembly withdraws the knife assembly from left to right as shown by the arrow. In this position, the latch 568 engages the distally located ramp 550 of the latch receiver 546. The roof 584 of the tunnel 552 prevents removal of the latch, thus the latch is able to pull the knife assembly through the longitudinal slit. FIG. 22F shows a stopped position wherein the knife actuating assembly has pulled the knife assembly back as far as it will go. A rib 586, formed as an integral part of the cartridge, does not allow the knife blade 536 to retract any further. FIG. 22G is a disengaged position wherein the latch receiver 546 has deflected the latch 568 upwardly as the latch rides up the distally located ramp 550. Notably, the proximal end 532 of the knife support 530 has emerged from the tunnels 552 at this point (see also FIG. 23) and the latch 568 is free to deflect upwardly. Since the knife assembly is held in position by the rib 586, the knife actuating assembly continues to move backwards (left to right) and disengages from the knife assembly which remains in the cartridge, as shown in FIG. 22H.

It will be appreciated from the foregoing description that the present invention describes a knife assembly that is an integral part of the disposable staple cartridge and also describes a reusable knife actuating assembly which stays with the reusable instrument. The knife actuating assembly includes a latch that is captured by a latch receiver in the knife assembly. As the knife actuating assembly moves forward, it bears against with the knife assembly and moves the knife forward to cut the tissue captured between the jaws. The knife assembly stays engaged to the knife actuating assembly as the latter is retracted until the knife assembly reaches its starting position, at which point the two assemblies unlatch and the knife actuating assembly is free to be further retracted out of the disposable staple cartridge.

The present invention eliminates the need for a rigid connection between the knife and its actuating mechanism. This permits the cartridge jaw to be articulated near the point where the knife connects with its actuating mechanism. Articulation at this location frees the jaw from simply rotating about a single pivot point and offers an opportunity to implement near-parallel jaw closure. The invention is particularly suitable in endoscopic or laparoscopic procedures wherein it is desired that the jaws open widely in an essentially parallel relationship while at the same time extending minimally beyond the end of the tubular frame of the surgical instrument.

Optionally, any of the devices described herein may include a blocking body as described in copending U.S. patent application Ser. No. 08/055,817, now U.S. Pat. No. 5,447,265, entitled, "Laparoscopic Surgical Instrument With a Mechanism For Preventing Its Entry Into the Abdominal Cavity Once It Is Depleted and Removed From the Abdominal Cavity", filed in the name of inventors Claude A. Vidal, Alan K. Plyley and Russel J. Redmond on Apr. 30, 1993. The entire contents of that application are herein expressly incorporated by reference.

It will, of course, be understood that modifications to the presently preferred embodiment will be apparent to those skilled in the art. Consequently, the scope of the present invention should not be limited by the particular embodiments discussed above, but should be defined only by the claims set forth below and equivalents thereof.

We claim:

1. A surgical instrument with articulated jaw structure for capturing tissue of a body, the surgical instrument comprising:

a frame having an outer end;

a first jaw having a proximal portion and a distal portion, the distal portion of the first jaw extending from the outer end of the frame;

a second jaw having a proximal portion and a distal portion, the distal portion of the second jaw extending from the outer end of the frame;

one of said first and second jaws having a staple cartridge for holding a plurality of staples adapted to be inserted in the tissue;

the proximal portions of the first and second jaws mounted to each other for movement in a substantially parallel relation between a fully open position wherein the distal portions of the jaws are separated for receiving tissue therebetween and an approximated position wherein the distal portions of the jaws are closer together for capturing said tissue, the jaws being in the fully open position when the distal portion of at least one of the jaws is located in an extended position away from the outer end of the frame and being in the approximated position when the distal portion of said one jaw is located in a retracted position closer to the outer end of the frame;

an actuating mechanism mounted to the frame, the actuating mechanism in operative engagement with the jaws for moving the jaws between the open and approximated positions;

both jaws being moveable between the extended and retracted positions;

the frame comprising a tubular frame and the proximal portions of the jaws being pivotally mounted to each other within the tubular frame about a pivot pin mounted within the tubular frame;

wherein the actuating mechanism has a cam and the proximal portions of the jaws each have a camming surface, the cam and camming surfaces configured such that upon movement of the cam between a first position and a second position, the jaws will pivot relative to each other between the open position and an intermediate position, respectively;

one of said jaws further having a cam stop for engaging the cam when the cam is in the second position such that upon further movement of the cam between the second position and a third position, the jaws retract within the tubular frame; and one of the jaws further comprising a ramp that is engageable with the outer end of the tubular frame upon movement of the jaws between the intermediate and approximated positions, the ramp configured such that the jaws move in a substantially parallel relation between the intermediate position and the approximated position upon movement of the cam between the second position and the third position, respectively.

2. The surgical instrument of claim 1 wherein the cam and camming surfaces are configured such that upon movement of the cam between the first and second positions, the jaws pivot without substantial axial movement between the open and intermediate positions, respectively.

3. The surgical instrument of claim 1 wherein the cam is axially moveable between the first and second positions and wherein the axial distance traversed by the cam in moving between the first and second positions is greater than the axial distance traversed by the jaws in moving between the open and intermediate positions.

4. The surgical instrument of claim 1 wherein the tubular member includes a collar mounted to the outer end of the tubular member, the collar having a pair of arms that are diametrically opposed within the tubular frame, each arm having a longitudinally extending slot with the pivot pin mounted for longitudinal movement within the slots.

5. The surgical instrument of claim 1 wherein the cam includes a traversely extending pin and the camming surface of the second jaw includes a diagonally extending surface of a slot defined by the second jaw, the diagonally extending surface extending proximally toward the first jaw.

6. A surgical instrument with articulated jaw structure for capturing tissue of a body, the surgical instrument comprising:

a frame having an outer end;

a first jaw having a proximal portion and a distal portion, the distal portion of the first jaw extending from the outer end of the frame;

a second jaw having a proximal portion and a distal portion, the distal portion of the second jaw extending from the outer end of the frame;

one of said first and second jaws having a staple cartridge for holding a plurality of staples adapted to be inserted in the tissue;

the proximal portions of the first and second jaws mounted to each other for movement in a substantially parallel relation between a fully open position wherein the distal portions of the jaws are separated for receiving tissue therebetween and an approximated position wherein the distal portions of the jaws are closer together for capturing said tissue, the jaws being in the fully open position when the distal portion of at least one of the jaws is located in an extended position away from the outer end of the frame and being in the approximated position when the distal portion of said one jaw is located in a retracted position closer to the outer end of the frame;

an actuating mechanism mounted to the frame, the actuating mechanism in operative engagement with the jaws for moving the jaws between the open and approximated positions;

a knife assembly having a knife blade defining a cutting edge, one of said jaws defining a longitudinal slit for receiving the knife assembly such that the cutting edge of the knife blade is permitted to move longitudinally in the slit when the jaws are in the approximated position; and a knife actuating mechanism mounted to the frame for moving the knife assembly between a first position adjacent a proximal end of the longitudinal slit and a second position located distally from the proximal end of the slit and a means for automatically disengaging the knife actuating mechanism from the knife assembly upon movement of the knife actuating mechanism to an unlatched position.

7. The surgical instrument of claim 6 wherein the knife assembly includes a bearing surface and a latch receiver and wherein the knife actuating mechanism includes a bearing surface and a latch, the bearing surface of the knife actuating mechanism being disposed against the bearing surface of the knife assembly for moving the knife assembly from the first position to the second position when the knife actuating assembly is moved distally from a first latched position to a second latched position, said latch being engageable with the latch receiver for moving the knife assembly from its second position to its first position when the knife actuating mechanism is moved proximally from its second latched position to its first latched position.

8. The surgical instrument of claim 7 wherein the one of said jaws includes a longitudinal cartridge defining said longitudinal slit for slideably receiving the knife assembly.

9. A surgical instrument with articulated jaw structure for capturing tissue of a body, comprising:

a tubular frame having an outer end;

an actuating mechanism movable inside the tubular frame, the actuating mechanism having a cam;

a first jaw having a proximal portion inside the tubular frame and a distal portion outside the tubular frame, the proximal portion defining a camming surface for engaging the cam;

a second jaw having a proximal portion inside the tubular frame and a distal portion outside the tubular frame, the second jaw pivotally mounted relative to the first jaw, the proximal portion of the second jaw also defining a camming surface for engaging the cam;

the cam and camming surfaces configured such that upon movement of the cam between a first position and a second position, the jaws pivot relative to each other between an open position and an intermediate position, respectively;

a cam stop disposed on one of said jaws for engaging the cam when the cam is in the second position such that upon further movement of the cam between the second position and a third position, the jaws move axially in the tubular frame; and one of said jaws further comprising a ramp that engages the outer end of the tubular frame upon axial retraction of the jaws, the ramp configured such that the jaws move in a substantially parallel relation between the intermediate position and an approximated position upon movement of the cam between the second position and the third position, respectively.

10. A surgical instrument with articulated jaw structure for capturing tissue of a body, comprising:

a first jaw and a second jaw, the first jaw having a tissue contacting surface;

a longitudinal cartridge detachably mounted to the second jaw, the longitudinal cartridge having a proximal end, a distal end and a tissue contacting surface;

the first jaw and the second jaw connected to one another to permit movement in a substantially parallel relation at least partially during movement between an open position wherein the tissue contacting surfaces are widely separated to receive tissue therebetween and an approximated position wherein the tissue contacting surfaces are in close proximity to and in opposed alignment with each other;

a knife assembly having a bearing surface, a latch receiver and a knife blade defining a cutting edge;

said longitudinal cartridge defining a longitudinal slit for slidably receiving said knife assembly such that the cutting edge of the knife blade is permitted to move longitudinally between the tissue contacting surfaces when the jaws are in the approximated position;

a knife actuating mechanism including a bearing surface and a latch, the bearing surface of the knife actuating mechanism being disposed against the bearing surface of the knife assembly for moving the knife assembly from a first position adjacent the proximal end of the cartridge to a second position located distally from the proximal end when the knife actuating assembly is moved distally from a first latched position to a second latched position, said latch being engageable with the latch receiver for moving the knife assembly from its second position to its first position when the knife actuating mechanism is moved proximally from its second latched position to its first latched position; and means for disengaging the latch from the latch receptacle when the knife actuating mechanism moves from the first latched position to an unlatched position.

* * * * *